United States Patent
Song et al.

(10) Patent No.: US 9,889,521 B2
(45) Date of Patent: Feb. 13, 2018

(54) METHOD AND SYSTEM FOR PULL TESTING OF WIRE BONDS

(71) Applicant: ASM Technology Singapore Pte Ltd, Singapore (SG)

(72) Inventors: Keng Yew Song, Singapore (SG); Yi Bin Wang, Singapore (SG); Qing Le Tan, Singapore (SG); Lin Wei Zheng, Singapore (SG); Jia Le Luo, Singapore (SG)

(73) Assignee: ASM TECHNOLOGY SINGAPORE PTE LTD, Singapore (SG)

(*) Notice: Subject to any disclaimer, the term of this patent is extended or adjusted under 35 U.S.C. 154(b) by 234 days.

(21) Appl. No.: 14/558,395

(22) Filed: Dec. 2, 2014

(65) Prior Publication Data
US 2016/0153880 A1    Jun. 2, 2016

(51) Int. Cl.
  *B23K 20/10*    (2006.01)
  *B23K 31/12*    (2006.01)
  *G01N 19/04*    (2006.01)

(52) U.S. Cl.
  CPC ............ *B23K 20/10* (2013.01); *B23K 31/125* (2013.01); *G01N 19/04* (2013.01); *H01L 2224/859* (2013.01)

(58) Field of Classification Search
  CPC ...... G01N 19/04; B23K 20/007; B23K 20/10; B23K 20/123; B23K 31/125
  See application file for complete search history.

(56) References Cited

U.S. PATENT DOCUMENTS

| | | | |
|---|---|---|---|
| 5,591,920 A * | 1/1997 | Price | B23K 31/125 228/4.5 |
| 5,660,319 A | 8/1997 | Falcone et al. | 228/110.1 |
| 6,467,678 B2 | 10/2002 | Mochida et al. | 228/180.5 |
| 6,564,115 B1 * | 5/2003 | Kinnaird | H01L 24/05 219/56.1 |
| 2007/0069207 A1 | 3/2007 | Yang et al. | 257/48 |
| 2011/0058979 A1 * | 3/2011 | Murai | B23K 35/3013 420/508 |

FOREIGN PATENT DOCUMENTS

| TW | 473884 B | 1/2002 |
|---|---|---|
| TW | I275166 B | 3/2007 |

* cited by examiner

*Primary Examiner* — David M Gray
*Assistant Examiner* — Andrew V Do
(74) *Attorney, Agent, or Firm* — Ostrolenk Faber LLP

(57) ABSTRACT

A method for pull testing a wire bond. The method including the steps of: (i) with a wire bonding tool, bonding an end of a wire to make a bond at a first location on a bonding surface having a conductive material, such that the bond completes an electrical circuit; (ii) clamping the wire with a wire clamp; (iii) pulling the wire with the wire clamp to apply a predetermined pulling force; (iv) detecting whether the electrical circuit is open; and (v) if the electrical circuit is open, determining that there has been a bond failure, and automatically incrementing a bond failure count.

28 Claims, 8 Drawing Sheets

METHOD AND SYSTEM FOR PULL TESTING OF WIRE BONDS

TECHNICAL FIELD

The present invention relates to pull testing of wire bonds.

BACKGROUND

Wire bonders are used during semiconductor assembly and packaging for making electrical interconnections between electrical contact pads on a semiconductor die and a substrate, or between electrical contact pads on different semiconductor dies. Wire is fed from a wire spool containing bonding wire to a bonding tool such as a capillary for performing wire bonding.

A typical method used to bond or weld the wire to a connection pad is through a combination of heat, pressure and/or ultrasonic energy. It is a solid phase welding process, wherein the two metallic materials (the wire and the pad surface) are brought into intimate contact. Once the surfaces are in intimate contact, electron sharing or inter-diffusion of atoms takes place, resulting in the formation of a wire bond. The two main types of wire bond are ball bonds and wedge bonds.

In order to ensure consistent wire bonding performance, it is desirable to assess portability of wire bonding apparatus as well as the robustness of the bonding recipe. Typically, in order to do so, bonding parameters such as ball size, ball thickness, ball shear, intermetallic coverage, occurrence of ball lift, and occurrence of bond pad peeling are measured, and compared across wire bonders and/or recipes.

One widely used test of bond quality is the pull test. In a pull test, a series of bonded wires extending between respective pairs of bond pads are each pulled manually by tweezers or a hook in direction generally away from the bond pads. Dedicated wire pulling machines specifically designed for this task are also known. Bonded wires subjected to pulling in this fashion may fail according to one of a number of failure modes, including ball lift (the ball completely lifts away from its bond pad), ball neck failure (the neck between the wire and the ball fractures), heel breakage (a fracture at the heel of a wedge bond), weld lift (a wedge bond completely lifts away from its bond pad), or bond pad lift (aluminium metallization on the bond pad peels off to expose the substrate). The number of occurrences of each type of failure is determined by manual inspection of the bonds under a microscope, and used as an indicator of bond quality.

Existing pull test methods have a number of shortcomings. If wires are pulled manually, it is difficult, if not impossible, to compare test results since the pulling force may vary dramatically across different persons, and even within or between tests conducted by a single person. If wires are pulled using a dedicated wire pull machine, the test can be very time consuming, especially if it is desired to test a large number of wires. In either case, visual inspection and counting of bond failures is required, this being a very time consuming and error-prone task, especially for large sample sizes.

There remains a need, therefore, for a pull test method and system which overcomes or alleviates at least one of the foregoing difficulties, or which at least provides a useful alternative.

SUMMARY

Certain embodiments of the invention relate to a method for pull testing of a wire bond, the method comprising steps of:

(i) with a wire bonding tool, bonding an end of a wire to make a first bond at a first location on a bonding surface comprising a conductive material, such that the first bond completes an electrical circuit;
(ii) clamping the wire;
(iii) applying a constant pulling force to the wire with the wire clamp;
(iv) detecting whether the electrical circuit is open; and
(v) if the electrical circuit is open, determining that there has been a bond failure, and automatically incrementing a bond failure count.

Other embodiments relate to a pull testing system for a wire bonder, the system comprising:

a wire bonding tool configured to receive a wire to bond the wire to a bonding surface comprising a conductive material;
at least one wire clamp;
an open circuit detector electrically connectable at respective terminals to the bonding surface and to the wire; and
a controller which is configured to:
(i) control the wire bonding tool to make a first bond between the wire and the bonding surface at a first location, such that the first bond completes an electrical circuit with the bonding surface, the wire and the open circuit detector;
(ii) control the wire clamp to clamp the wire;
(iii) move the wire clamp to apply a constant pulling force to the wire;
(iv) receive a detection signal from the open circuit detector indicating whether the electrical circuit is open; and
(v) if the electrical circuit is open, determine that there has been a bond failure, and automatically increment a bond failure count.

The first bond may be a ball bond or a wedge bond.

In some embodiments, the pulling force is applied in a direction normal to the bonding surface.

In some embodiments the method further comprises, if the electrical circuit is open after step (iv), adjusting a bonding power of the wire bonding tool; and making a further bond at the bonding surface at the first location.

The method may further comprise making a second bond at the bonding surface at a second location. The second bond may be a wedge bond.

The method may further comprise, prior to clamping the wire, translating the position of the wire bonding tool to feed out a predetermined additional length of wire. Said translation may comprise a lateral translation and a vertical translation. Alternatively, said translation may comprise a vertical translation. Said vertical translation may be less than a distance between the first location and a second location on the bonding surface; and the method may further comprise making a second bond at the second location, whereby the pulling force is applied to the wire.

In some embodiments the method comprises:
initializing the bond failure count; and
then, performing successive iterations of steps (i) to (v) to determine a bond failure percentage.

The method may further comprise:
adjusting a value of a bonding parameter of the wire bonding tool;
re-initializing the bond failure count; and
continuing to perform successive iterations of steps (i) to (v) to determine a further bond failure percentage.

Some embodiments comprise generating a plurality of bond failure percentages, respective bond failure percentages corresponding to respective values of the bonding parameter.

BRIEF DESCRIPTION OF THE DRAWINGS

Embodiments of the invention will now be described, by way of non-limiting example only, with reference to the accompanying drawings in which.

DETAILED DESCRIPTION

Embodiments of the invention provide a method and system of pull testing in which the number of bond failures (due to, for example, ball lifts or bond pad peeling) is registered without requiring manual inspection. The method may advantageously use existing wire bonding equipment to automatically perform wire pulling and counting of any consequent bond failures. No human interference is required to handle the sample. The method is fast and accurate, and able to test a large number of wire bonds in a relatively short time.

In general terms, the method may comprise using a spooled wire to form a series of pairs of bonds to make interconnects between two locations on a bonding surface. Typically, the first bond is a ball bond and the second bond is a wedge bond. During formation of each interconnect, the wire is pulled after formation of the first bond, using the same equipment as used to form the bond, and a sensor automatically detects whether there is a ball lift or bond pad peel event, following which the second bond is formed to complete the interconnect. This sequence is repeated multiple times, and the number of ball lift/bond pad peel events counted automatically to provide a measure of bond quality.

Figure 1:
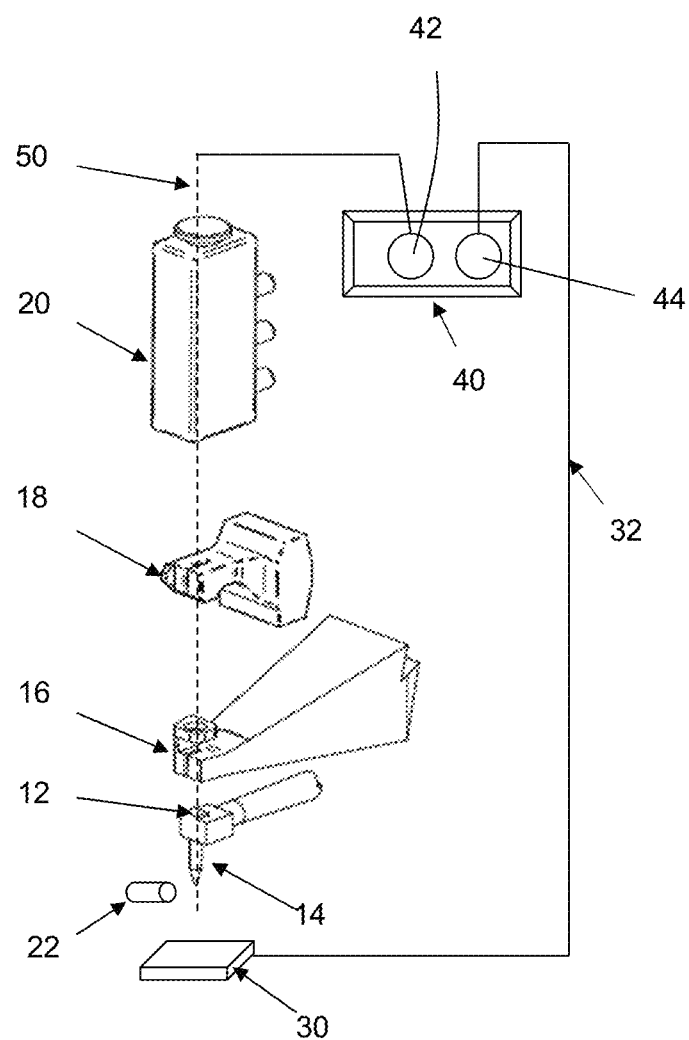
FIG. 1 is a schematic view of a system for pull testing according to embodiments of the invention.
Figure 2:
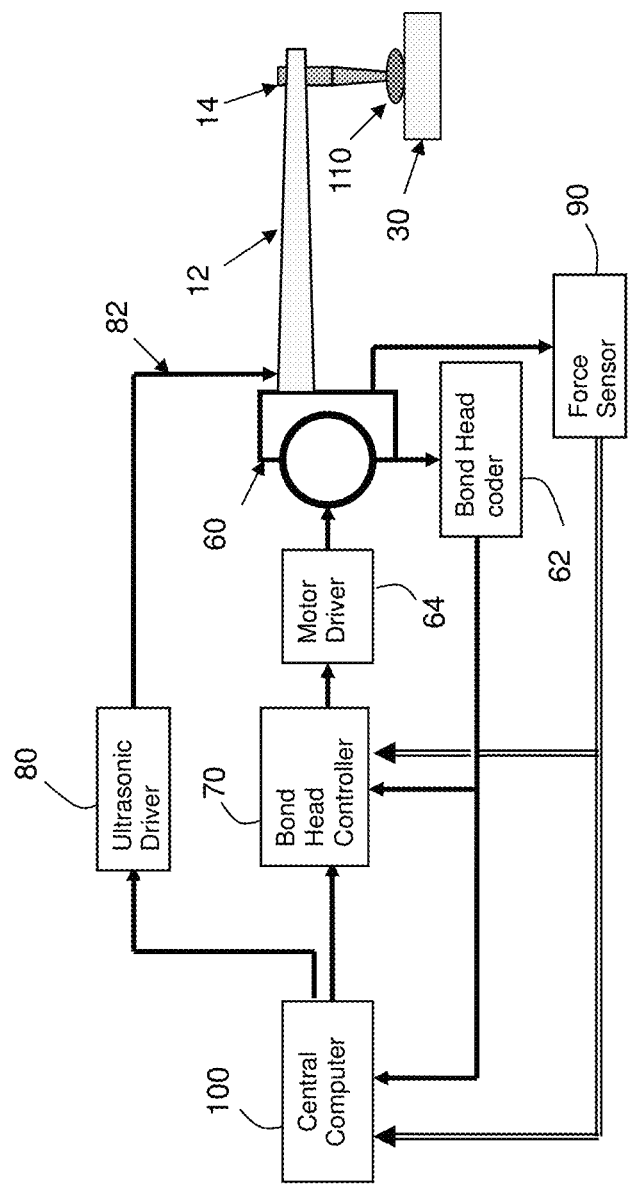
FIG. 2 is a further schematic view of part of the system of FIG. 1.

Referring initially to FIG. 1 and FIG. 2, there is shown a schematic depiction of a system 10 for pull testing according to an embodiment of the present invention. The system 10 comprises standard wire bonding equipment including a wire bonding tool comprising an ultrasonic transducer 12 operably coupled to a capillary 14, a wire clamp 16 positioned above the capillary 14 for clamping a wire 50 fed through the capillary, and an air tunnel 20 for controlling the tension in the wire 50. Optionally, a second wire clamp 18 may be employed. The system 10 comprises an electrical flame-off torch 22 for forming a free air-ball.

As shown in FIG. 2, the transducer 12 of the wire bonding tool is connected to a bond head 60 having a motor (not shown) which is driven by motor driver 64 under the control of bond head controller 70. Bond head controller 70 is in communication with a computer system 100, which is responsible for overall control and monitoring of the system 10 and which sends control signals to bond head controller 70 to move the bond head 60 to a desired position. The bond head is operably coupled to a bond head encoder 62 which sends position data, and to a force sensor 90 which sends bond head force data, back to computer system 100. The position data represent a current position of the bond head while the bond head force data represent the force being applied by bond head 60, via the tip of capillary 14, to a ball 110 at bond pad 30. Computer system 100 also sends control signals to ultrasonic driver 80 to cause it to transmit an ultrasonic control current 82 to the transducer 12 such that the transducer 12 vibrates to produce a desired amount of ultrasonic energy for the bonding process.

The system 10 comprises a wire clamp driver (not shown) for controlling the opening and closing of wire clamp 16 and second wire clamp 18, under the control of computer system 100. Also provided as part of system 10, but not depicted in the drawings, are at least one motor and associated driver, in communication with computer system 100, used to move wire clamp 16 and/or wire clamp 18. For example, the wire clamp 16 may be attached to the transducer 12 for coordinated movement with the transducer 12, while the second wire clamp 18 may be fixed in position.

The computer system 100 may be a commercially available computer system such as a 32-bit or 64-bit Intel Architecture-based computer system, including standard computer components, including random access memory (RAM), at least one processor, a storage device (such as a hard disk drive or solid state storage device) and external interfaces, all interconnected by a bus. The external interfaces include universal serial bus (USB) interfaces, at least one of which may be connected to a keyboard or a pointing device such as a mouse, a network interface connector (NIC) which connects the system 100 to a communications network, and a display adapter, which is connected to a display device such as an LCD panel display. The system 100 has stored on the storage device a number of standard software modules, including an operating system such as Linux or Microsoft Windows.

Also stored on the storage device is a bonding control module which receives input data from sensors, such as the position data and bond head force data, as well as input data corresponding to a desired sequence of movements of the bond head 60, transducer 12 and wire clamp 16. The outputs of the bonding control module are control signals which are transmitted to actuators of the various mechanical system components (e.g., the bond head controller 70, ultrasonic driver 80, wire clamp driver, etc.). The storage device also comprises a bond failure detection module which provides sequences of bonding processes to the bonding control module, receives signals indicative of bonding failures, and monitors the number of bonding failures during a bond failure detection process.

Returning to FIG. 1, the system 10 comprises an open circuit sensor 40 for detecting whether there is an open circuit in the system. The open circuit sensor 40 is in communication with computer system 100. A first terminal 42 of the sensor module 40 is electrically connected to the wire 50, and a second terminal 44 of open circuit sensor 40 is electrically connected to a conductive surface of the bond pad 30 by cable 32. Accordingly, when the exposed end of wire 50 is welded to the bond pad 30 to form a wedge bond or ball bond at a first location on the bond pad 30, an electrical circuit (formed by the wire 50, bond pad 30, sensor module 40 and cable 32) is completed. If the connection between the wire 50 and bond pad 30 is broken, for example due to a ball lift during a pull test (as will later be described), the open circuit sensor 40 detects an open circuit, and sends a bond failure detection signal to the bond failure detection module of computer system 100.

Figure 3:
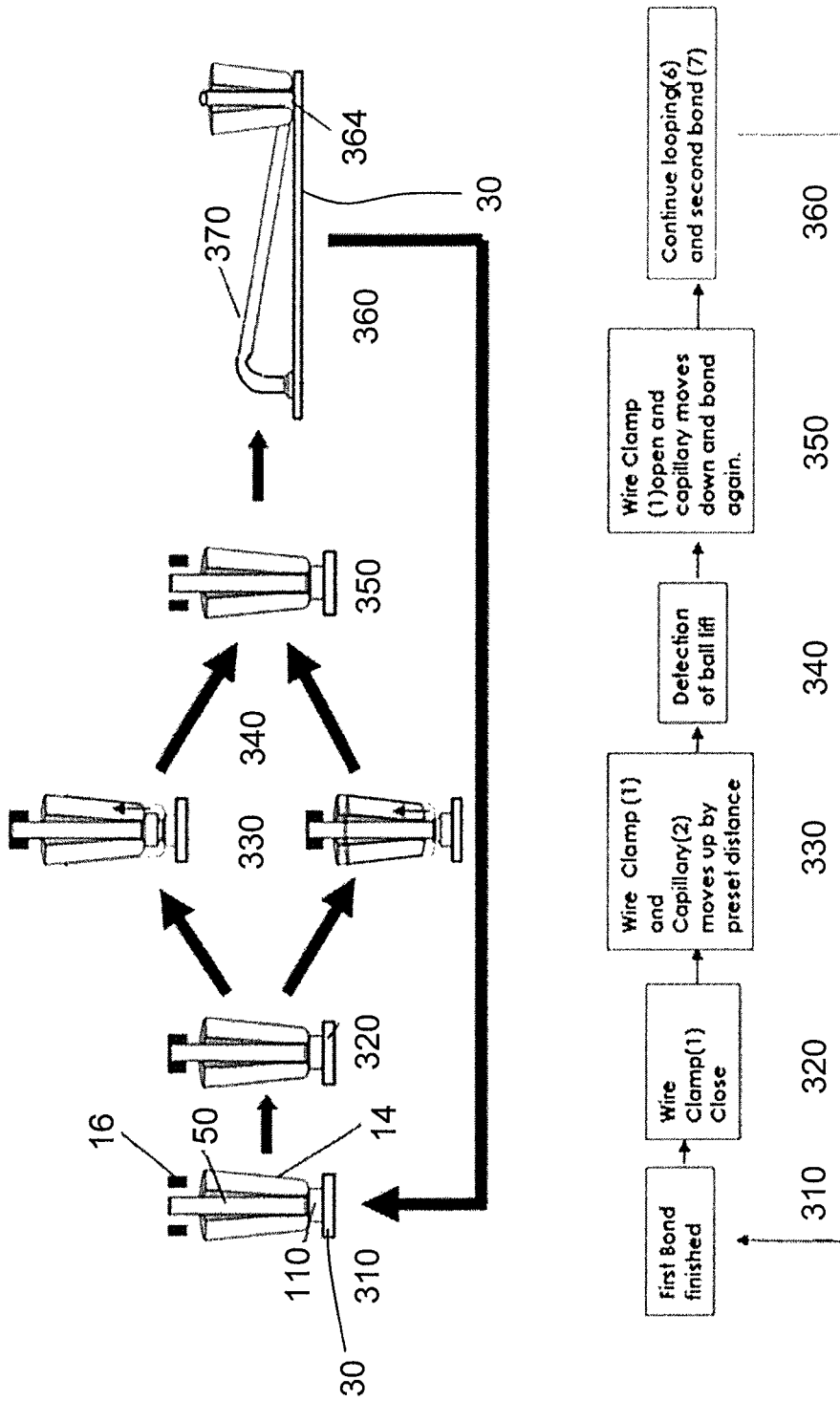
FIG. 3 illustrates the process sequence in a method of pull testing according to embodiments of the invention.

Turning now to FIG. 3, there is shown a schematic illustration of a first pull testing method. The illustrated method is performed multiple times in order to generate statistics relating to bond quality. A bond failure count is maintained by the bond failure detection module of computer system 100, and is automatically updated in response to a detection of a bond failure by open circuit sensor 40. The bond failure count is initialized to zero at the start of each test.

At 310, wire clamp 16 is open, and the capillary 14 descends towards bond pad 30 to form a ball bond by applying force and ultrasonic energy (via transducer 12) to ball 110 in known fashion. The bonding process may be characterized by bonding parameters including the free air ball (FAB) size, the ultrasonic power (as determined by the current, in mA, delivered to the transducer 12), and the force applied to the ball by the capillary tip.

Next, at 320, the wire clamp 16 is closed to clamp the wire 50. Then, at 330, the wire clamp 16 and capillary 14 are moved in a generally upward direction, away from the bond pad 30. The upward movement is by a predetermined distance, so as to apply a predetermined pulling force to the wire.

The pulling force can be approximated using Young's modulus, as follows:

$$F = \frac{EA_0 \Delta L}{L_0},$$

where E is the Young's modulus of the wire 50, $A_0$ is its cross-sectional area, $L_0$ is the original wire length (the length of wire between the clamp 16 and the bond pad 30), and $\Delta L$ is the change in length of the wire, i.e., the predetermined pulling distance. For example, for a PdCu wire (E=117 GPa) having 20 um diameter and a clamp-bond pad length ($L_0$) of 17 mm, a predetermined pulling distance of 100 um will result in a pulling force of 0.216 N.

Accordingly, given known characteristics of the wire used in the bonding process, it is possible to apply approximately the same pulling force in different pull tests, such that results from the different tests are directly comparable. The pulling force used in the testing procedure may be chosen based on characteristics of the wire, for example the wire diameter and/or the material of the wire.

The pulling force may be applied for a predetermined time which depends on the desired pulling speed (e.g., 10 um/ms). After the predetermined time, the bonded ball 110 may be lifted from the bond pad 30 due to the pulling force, depending on the quality of the ball bonding to the bond pad 30. If the ball 110 is lifted, this breaks the electrical circuit (FIG. 1) and the open circuit sensor 40 thereby detects the open circuit, sending a positive detection signal to computer system 100, which increments the bond failure count.

In some embodiments, failure modes other than ball lift may occur, depending on the parameters of the bonding process. For example, if excessive force and/or ultrasonic energy are applied to the ball during bonding, this may result in an increased risk of bond pad peeling. Since bond pad peeling will also result in a disconnection of the wire from the bond pad 30 during the pull test, it will also cause the bond failure count to be incremented by the bond failure detection module, due to detection of the resultant open circuit. Similarly, a ball neck fracture will result in a positive detection.

At step 340, if a positive detection signal has been received, computer system 100 causes wire clamp 16 to be opened, and the capillary 14 moves down to the bond pad 30 again to form a further bond at the same location (step 350). Optionally, a higher bond force and/or ultrasonic control current may temporarily be used for the further bond, to ensure that a further ball lift event will not occur during subsequent steps in the sequence.

At step 360, if no positive detection signal has been received, or if a further bond has been completed, the sequence is completed by keeping the clamp 16 open, moving the capillary 14 upwards to a height sufficient to feed enough wire to form a wire loop 370, moving the capillary 14 to a second location on the bond pad 30, and forming a second bond in the form of wedge bond 364. The trajectory followed by the capillary in forming the wire loop 370 and wedge bond 364 is identical to the trajectory that would ordinarily be followed in a wire bonding process where no pull testing is performed. Advantageously, therefore, the pull test can be readily accommodated by insertion as an intermediate sequence in existing control processes. The wedge bond is completed in known fashion by feeding a desired length of wire through the capillary 14, and then clamping the wire and pulling it away from the bond pad 30 to leave a free tail dangling from the capillary in readiness for formation of the next ball bond.

Steps 310 to 360 are repeated to form a plurality of pairs of bonds, each of which has undergone a pull test after formation of the first bond. At this point, it is possible to determine the percentage of bond failures (bond failure count/total number of tested bonds), to be used as a proxy for bond quality.

Figure 7:
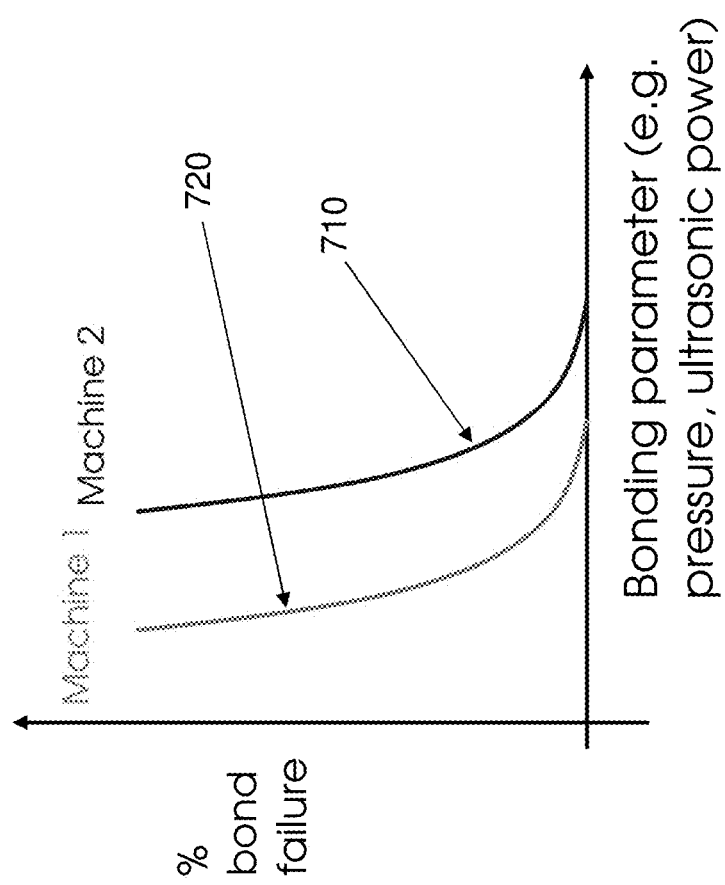
FIG. 7 shows exemplary bond failure percentage v. bonding parameter curves.

The bonding parameters may be adjusted, and the test repeated for each different set of bonding parameters, so as to determine bond failure percentage as a function (or series of functions) of the bonding parameters. This is illustrated schematically in FIG. 7, which shows two example curves 710, 720 of bond failure percentage plotted as a function of a bonding parameter, for example bond force or ultrasonic control current. Curve 710 shows the dependence of bond failure percentage on the bonding parameter for a first wire bonding machine, and curve 720 for a second wire bonding machine. In general, the bond failure percentage curve will vary for different wire bonding machines, but will typically be of the same or very similar shape, but translated along the x-axis (i.e., the parameter axis). The curve generated for one machine may therefore be used as a reference for other machines. In particular, one machine may be chosen as a reference machine, and after testing is carried out on a subsequent machine to generate a curve such as curve 710 or curve 720, the bonding parameter or bonding parameters may be adjusted so that the curve for the subsequent machine matches the curve for the reference machine.

By generating a bond failure v. ultrasonic power curve for a wire bonding machine, it is possible to determine a minimum ultrasonic power which must be used in order to ensure that a zero bond failure level is achieved. In the semiconductor industry, it is generally a requirement that a bonding recipe have zero bond failure for a given sample size, due to stringent manufacturing quality requirements.

Figure 8:
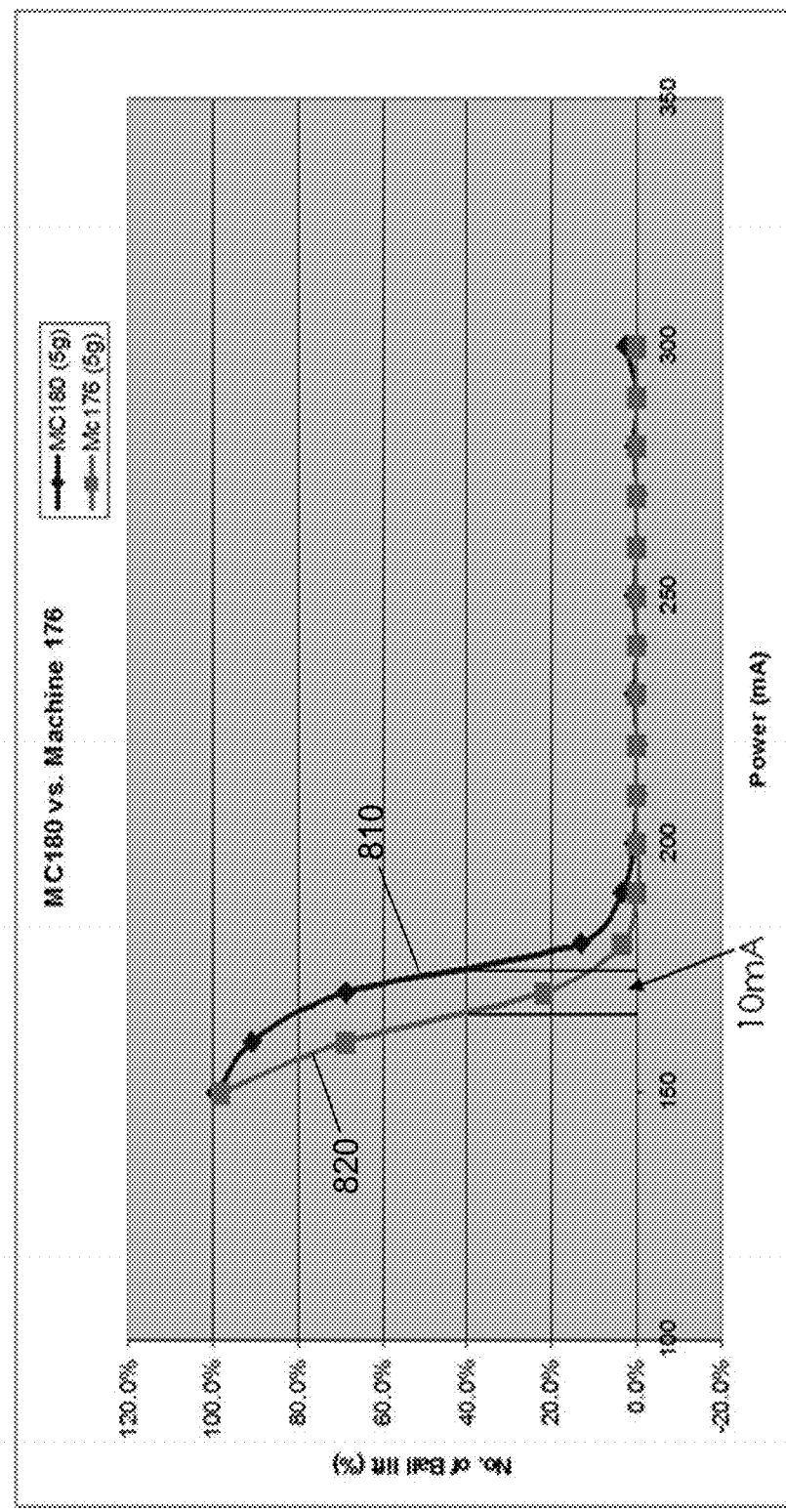
FIG. 8 shows bond failure percentage v. ultrasonic power curves for two different bonding machines, generated by a method according to embodiments of the invention.

The variation between wire bonding machines is exemplified in FIG. 8, which shows a bond failure v. ultrasonic power curve for a first machine 810 and for a second machine 820. The curve 810 for the first machine is shifted by approximately 10 mA to the right relative to the curve 820 for the second machine. Accordingly, in order to ensure that there is zero bond failure for the first machine, a minimum power which is at least 10 mA greater than the minimum power for the second machine should be used.

Figure 4:
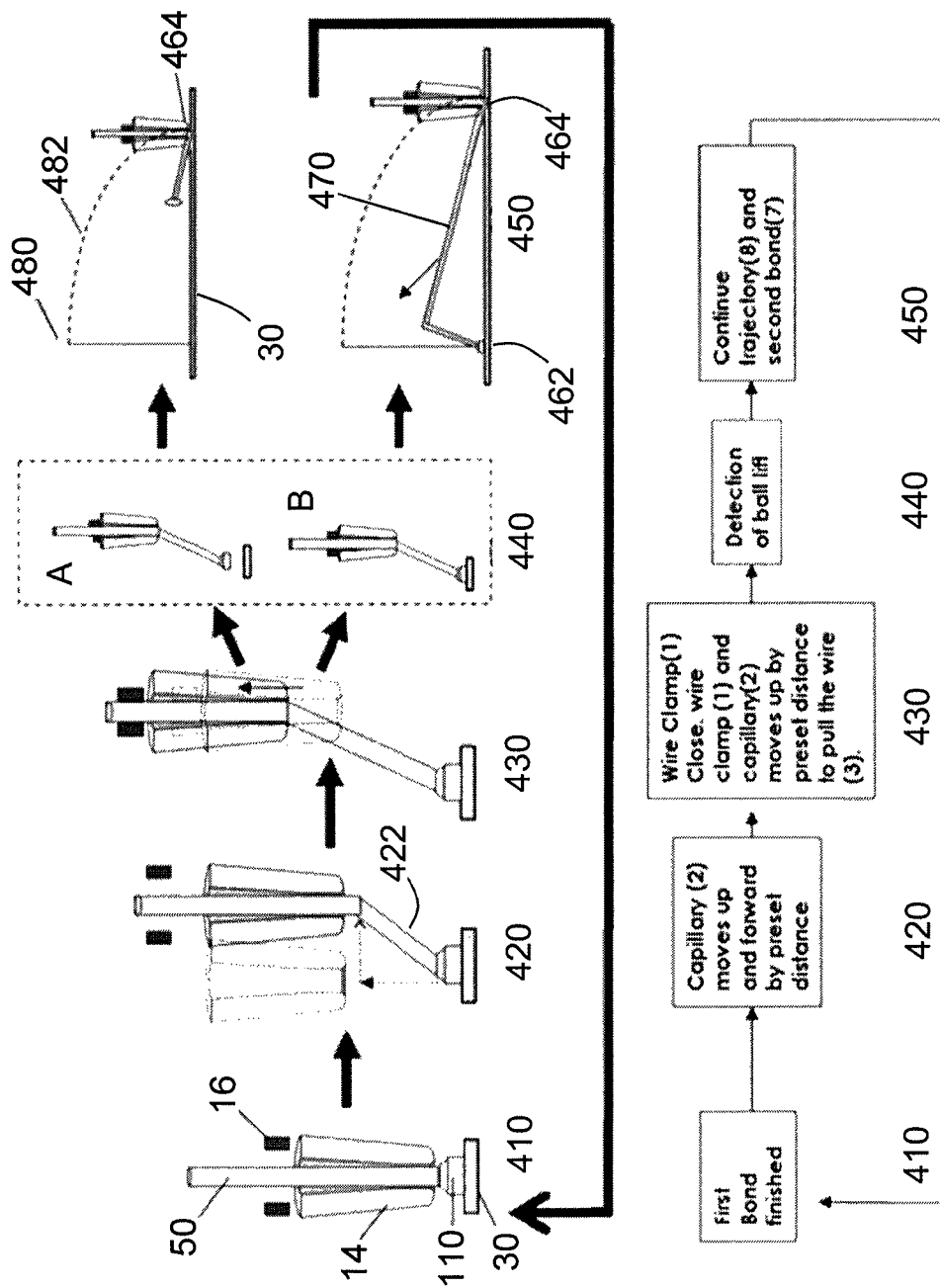
FIG. 4 depicts a method according to alternative embodiments.

In a second pull testing method, illustrated in FIG. 4, the capillary 14 is translated laterally (i.e., in the xy-plane) as well as vertically in order to create an angled section of wire of a certain length between the bond and the capillary tip, prior to applying the pulling force. The translation may comprise successive translations (e.g., vertical followed by lateral), or may be a single angled movement of the capillary.

In particular, at step 410 the capillary 14 is pressed against the ball 110 to form a ball bond 462 on bond pad 30 as before. Next, at step 420, the capillary 14 moves at a certain angle to pay out a desired length of wire 422.

At step 430, the wire clamp 16 is closed to clamp the wire 50. The capillary 14 and clamp 16 are then moved up a predetermined distance, in order to apply a desired pulling force substantially as discussed previously. After step 430, the bonded ball 462 will either have been lifted from the bond pad 30 (case A), or remain welded to it (case B), depending on the bond quality. If a ball lift event occurs, the open circuit sensor 40 detects the open circuit and sends a positive detection signal to computer system 100 as before, such that a ball failure count is automatically incremented at the computer system 100.

In either case, at step 450 the capillary 14 is then moved to a predetermined height 480 corresponding to the desired length of interconnect loop 470, and is then moved along a curved path 482 to a second location on the bond pad 30, at which a second (wedge) bond 464 is then formed. On completion of the bond, the wire is torn away from the bond pad 30 in order to prepare for the next pair of bonds as described earlier.

Figure 5:
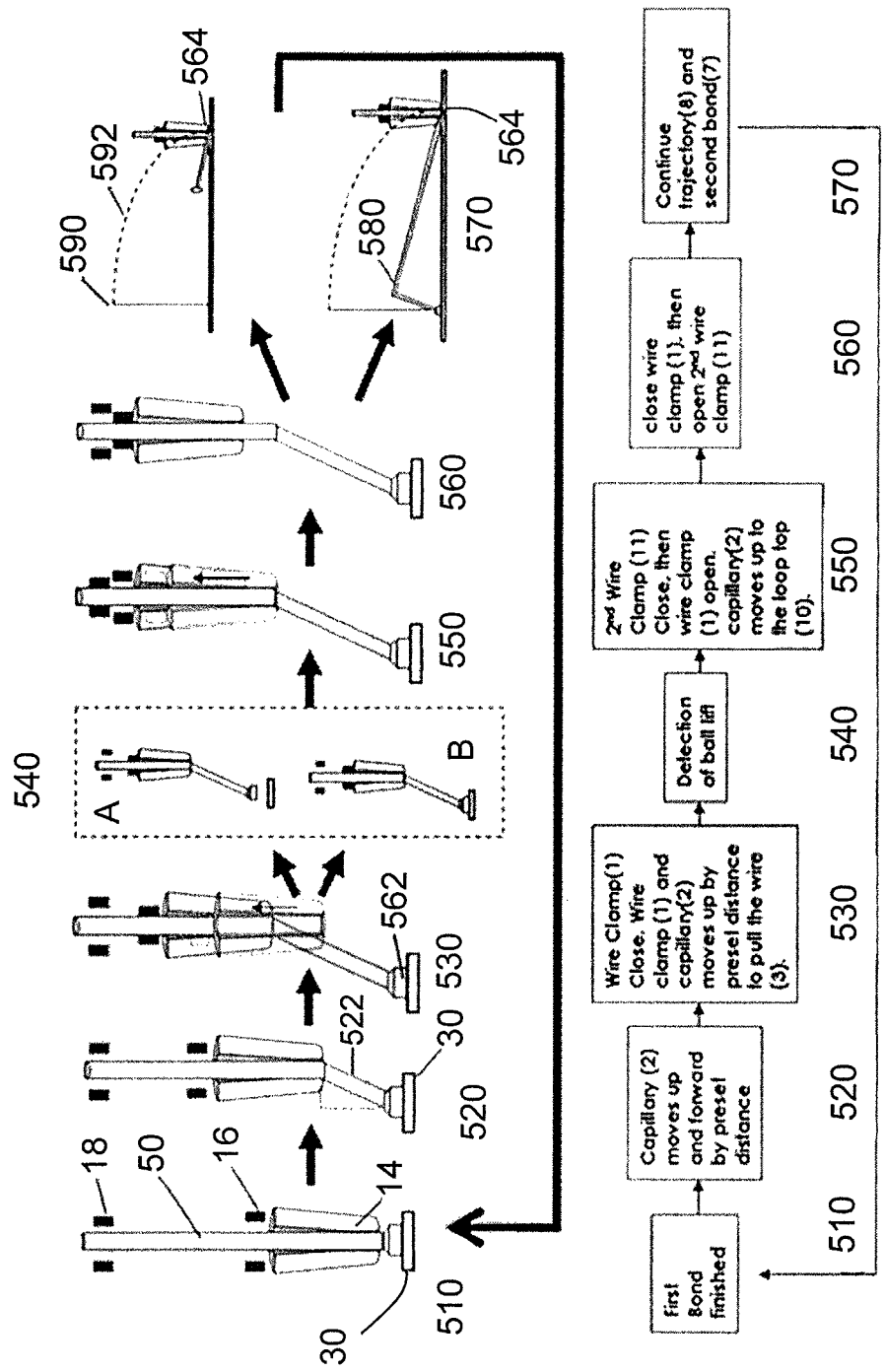
FIG. 5 depicts a method according to further embodiments.

In a third method, shown in FIG. 5 which illustrates a modified version of the method of FIG. 4, a second clamp 18 may advantageously be used to improve bonding stability, and reduce the risk of wire fly-away. In the unlikely event that the wire is broken at the tip of the capillary due to the pulling force, the terminating wedge bond at the second location on the bond pad cannot be performed successfully. By using a second wire clamp 18, additional wire can be paid out during step 550, thus ensuring that a successful bond can be completed at the second location.

At step 510, both clamps 16, 18 are open and a ball bond is formed on bond pad 30 as previously described.

Then, at step 520, the capillary 14 is moved at a certain angle (for example, by a vertical translation followed by a lateral translation) to pay out a desired length of wire 522.

At step 530, first wire clamp 16 is closed, and the first wire clamp 16 and capillary 14 are moved up a predetermined distance, in order to apply a desired pulling force substantially as discussed previously. After step 530, the bonded ball 562 will either have been lifted from the bond pad 30 (case A), or remain welded to it (case B), depending on the bond quality. If a ball lift event occurs, the open circuit sensor 40 detects the open circuit (step 540) and sends a positive detection signal to computer system 100 as before, such that a ball failure count is automatically incremented at the computer system 100.

At step 550, the second clamp 18 is closed, and the first clamp 16 then opened. The capillary 14 is moved to a predetermined height 590 corresponding to the desired interconnect loop 580 length. Then, at step 560, the first wire clamp 16 is closed, followed by opening the second wire clamp 18.

At step 570, the capillary 14 is moved along a curved path 592 to a second location on the bond pad 30, at which a second (wedge) bond 564 is then formed. On completion of the bond, the wire is torn away from the bond pad 30 in order to prepare for the next pair of bonds as described earlier.

Figure 6:
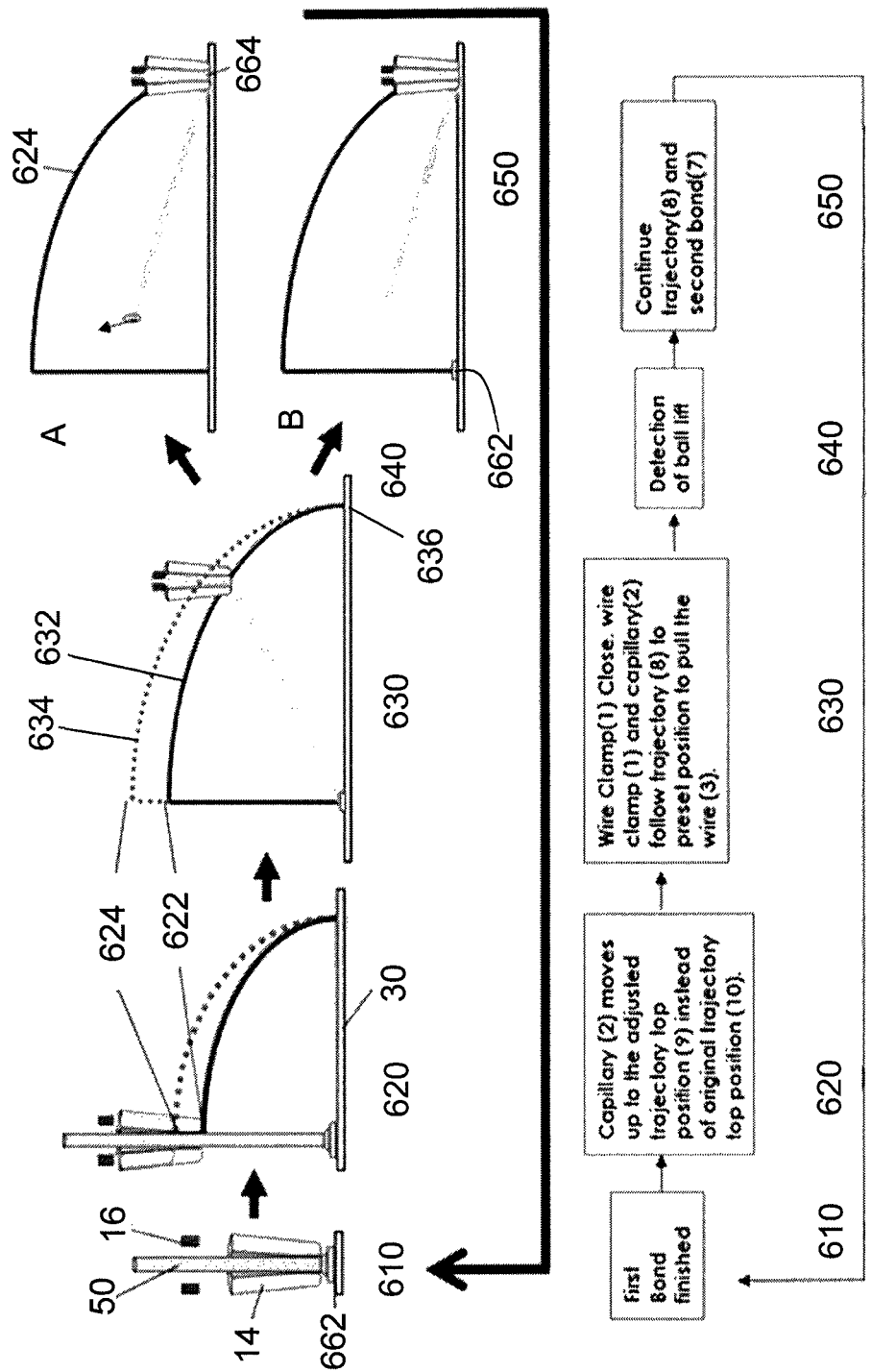
FIG. 6 depicts a method according to yet further embodiments.

A fourth pull testing method is shown in FIG. 6. In this method, the pulling force is generated by artificially shortening the length of wire used to create the wire loop between the first and second bonds.

More particularly, at step 610 a ball bond 662 is formed at a first location using capillary 14 as before. Next, at step 620, the capillary 14 is moved to a height 622, which is below the height 624 to which it would ordinarily be moved to form a second bond at a second location 636 on the bond pad 30.

The effect of the height difference is to produce a flatter trajectory 632 of the capillary tip than the expected trajectory 634, such that the capillary tip 14 must still traverse the same lateral distance between the first and second locations, but with a shorter length of wire between the ball bond 662 and the closed clamp 16. This results in a pulling force being applied to the wire, and consequently the ball bond (step 630). The pulling force will, in general, depend on the difference between heights 622 and 624.

Two exemplary failure modes are shown at 640; in case A, a ball lift event has occurred, while in case B a ball neck breakage has occurred. In either case, or if there is no bond failure, at step 650 a second bond 664 can be completed in order to finish the sequence, and a tail created for the next ball bond in the sequence as described previously. If a ball lift or ball neck breakage event occurs, then as before, the open circuit sensor 40 detects the open circuit and sends a positive detection signal to computer system 100, such that a ball failure count is automatically incremented at the computer system 100.

In the second, third and fourth methods, as for the first method, the sequence of operations can be repeated so as to form a plurality of pairs of bonds, each of which has undergone a pull test after formation of the first bond. At this point, it is possible to determine the percentage of bond failures (bond failure count/total number of tested bonds), to be used as a proxy for bond quality. The bonding parameters may be adjusted, and the test repeated for each different set of bonding parameters, so as to determine bond failure percentage as a function (or series of functions) of the bonding parameters.

At least some of the test methods described above (e.g., the second, third and fourth methods) can be used to determine an optimal process window for a wire bonder. For example, a series of tests with progressively increasing ultrasonic power can be run, and the bond failure percentage at each power setting recorded. At lower power settings, bond failures will tend to be due to ball lift events. As the power increases, the ball lift occurrence will eventually drop to zero. However, if power is increased to a sufficient level, bond pad peeling events will start to occur due to the much higher bonding strength between the ball and the bond pad. Accordingly, by determining the respective power settings at which ball lift events stop and bond pad peeling events start, an optimal process window can be defined.

In each of the above-described embodiments, a large number of bonds can be created and tested sequentially in automated fashion, since the pull test is inserted as an intermediate step in a conventional bonding sequence.

Advantageously, the method can be implemented with a simple hardware modification (adding an open circuit detector to conventional wire bonding hardware) in conjunction with a straightforward modification of the instructions issued by computer system 100.

The processes described above can provide a fast and easy assessment of bonding quality. As a large number of samples is able to be processed in a relatively short time, the dependence of bond failure percentage on bonding factors such as ultrasonic vibration, pressure, time, temperature, and free air ball size can be easily determined.

Although particular embodiments of the invention have been described in detail, many modifications and variations are possible within the scope of the invention, as will be clear to a skilled reader.

The invention claimed is:

1. A method for pull testing of a wire bond, the method comprising steps of:
    (i) with a wire bonding tool, bonding an end of a wire to make a first bond at a first location on a bonding surface comprising a conductive material, such that the first bond completes an electrical circuit;
    (ii) clamping the wire with a wire clamp;
    (iii) applying a constant predetermined pulling force to the wire with the wire clamp by moving the wire clamp away from the first bond by a predetermined distance in a predetermined direction to a second location spaced from the first location in a single continuous motion;
    (iv) detecting whether the electrical circuit is open when the wire bonding tool is at the second location; and
    (v) if the electrical circuit is open, determining that there has been a bond failure, and automatically incrementing a bond failure count; and thereafter
    (vi) forming a second bond at the bonding surface at a third location.

2. The method according to claim 1, wherein the first bond is a ball bond.

3. The method according to claim 2, wherein the pulling force is applied in a direction normal to the bonding surface.

4. The method according to claim 2, further comprising, if the electrical circuit is open after step (iv), adjusting a bonding power of the wire bonding tool;
    and making a further bond at the bonding surface at the first location.

5. The method according to claim 1, wherein the second bond is a wedge bond.

6. The method according to claim 1, further comprising, prior to clamping the wire, translating the position of the wire bonding tool to feed out a predetermined additional length of wire.

7. The method according to claim 6, wherein said translation comprises a lateral translation and a vertical translation.

8. The method according to claim 6, wherein said translation comprises a vertical translation.

9. The method according to claim 8, wherein said vertical translation 5 is less than a distance between the first location and a second location on the bonding surface; and
    wherein the method further comprises making a second bond at the second location,
    whereby the pulling force is applied to the wire.

10. The method according to claim 1, comprising:
    initializing the bond failure count; and then,
    performing successive iterations of steps (i) to (v) to determine a bond failure percentage.

11. The method according to claim 10, further comprising:
    adjusting a value of a bonding parameter of the wire bonding tool;
    re-initializing the bond failure count; and
    continuing to perform successive iterations of steps (i) to (v) to determine a further bond failure percentage.

12. The method according to claim 11, comprising generating a plurality of bond failure percentages, respective bond failure percentages corresponding to respective values of the bonding parameter.

13. The method according to claim 11, wherein the bonding parameter is selected from the group consisting of: bonding force; ultrasonic power; and free airball (FAB) size.

14. The method according to claim 1, wherein the second location is at a distance from the first location, which is not subsequently increased by moving the wire clamp, clamping the wire, away from the first bond beyond the predetermined distance in the predetermined direction.

15. A pull testing system for a wire bonder, the system comprising:
    a wire bonding tool configured to receive a wire to bond the wire to a bonding surface comprising a conductive material;
    at least one wire clamp;
    an open circuit detector electrically connectable at respective terminals to the bonding surface and to the wire; and
    a controller which is configured to:
    (i) control the wire bonding tool to make a first bond between the wire and the bonding surface at a first location, such that the first bond completes an electrical circuit with the bonding surface, the wire and the open circuit detector;
    (ii) control the wire clamp to clamp the wire;
    (iii) move the wire clamp away from the first bond by a predetermined distance in a predetermined direction to a second location spaced from the first location in a single continuous motion to apply a constant predetermined pulling force to the wire;
    (iv) receive a detection signal from the open circuit detector indicating whether the electrical circuit is open; and
    (v) if the electrical circuit is open, determine that there has been a bond failure, and automatically increment a bond failure count; and thereafter
    (vi) form a second bond at the bonding surface at a third location.

16. The system according to claim 15, wherein the first bond is a ball bond.

17. The system according to claim 16, wherein the controller is configured to move the wire clamp to apply the pulling force in a direction normal to the bonding surface.

18. The system according to claim 16, wherein the controller is configured to, on receiving an indication that the electrical circuit is open, adjust a bonding power of the wire bonding tool; and to control the wire bonding tool to make a further bond at the bonding surface at the first location.

19. The system according to claim 15, wherein the second bond is a wedge bond.

20. The system according to claim 15, wherein the controller is further configured to, prior to controlling the wire clamp to clamp the wire, translate the position of the wire bonding tool to feed out a predetermined additional length of wire.

21. The system according to claim 20, wherein said translation comprises a lateral translation and a vertical translation.

22. The system according to claim 20, wherein said translation comprises a vertical translation.

23. The system according to claim 22, wherein said vertical translation is less than a distance between the first location and a second location on the bonding surface; and wherein the controller is further configured to control the wire bonding tool to make a second bond at the second location, whereby the pulling force is applied to the wire.

24. The system according to claim 15, wherein the controller is further configured to:
   initialize the bond failure count; and then,
   perform successive iterations of steps (i) to (v) to determine a bond failure percentage.

25. The system according to claim 24, wherein the controller is further configured to:
   adjust a value of a bonding parameter of the wire bonding tool;
   re-initialize the bond failure count; and
   continue to perform successive iterations of steps (i) to (v) to determine a further bond failure percentage.

26. The system according to claim 25, wherein the controller is configured to generate a plurality of bond failure percentages, respective bond failure percentages corresponding to respective values of the bonding parameter.

27. The system according to claim 25, wherein the bonding parameter is selected from the group consisting of: bonding force; ultrasonic power; and free airball (FAB) size.

28. The system according to claim 15, wherein the second location is at a distance from the first location, which is not subsequently increased by moving the wire clamp, clamping the wire, away from the first bond beyond the predetermined distance in the predetermined direction.

* * * * *